United States Patent [19]

Brouwer et al.

[11] Patent Number: 4,664,694
[45] Date of Patent: May 12, 1987

[54] SUBSTITUTED THIAZOLIDINONES USEFUL AS PLANT GROWTH REGULATORS

[75] Inventors: Walter G. Brouwer, Wellington, Canada; Allen R. Blem, New Haven, Conn.

[73] Assignees: Uniroyal Chemical Company, Inc., Middlebury, Conn.; Uniroyal Ltd., Don Mills, Canada

[21] Appl. No.: 726,533

[22] Filed: Apr. 24, 1985

[51] Int. Cl.$^4$ .................. A01N 43/78; C07D 277/04; C07D 277/06

[52] U.S. Cl. .......................................... 71/90; 71/91; 548/182; 548/183

[58] Field of Search .................. 548/182, 183; 71/91, 71/90

[56] References Cited

U.S. PATENT DOCUMENTS 3,006,919 10/1961 Gaul et al. ........................ 548/182
3,853,902 12/1974 Raasch ............................. 548/182
4,019,892 4/1977 Pilgram ............................. 71/88

FOREIGN PATENT DOCUMENTS 0004129 9/1979 European Pat. Off. .
1500474 9/1967 France .............................. 548/183
1153486 5/1969 United Kingdom ............... 548/183
1345159 6/1971 United Kingdom .

OTHER PUBLICATIONS

Kigasawa et al., Chemical Abstracts, vol. 92: 146785f, 1980.
Girard et al., Chemical Abstracts, vol. 70:28269p, 1969.
Kametani et al., Heterocycles, vol. 9, No. 7, pp. 831-840, 1978.
Girard et al., Bull. Soc. Chim. Fr. 1968, (8), pp. 3477-3483, (1968).
Monatsche Fur Chemie, 49, 1928, Andreasch, p. 122-132.

Primary Examiner—Donald G. Daus
Assistant Examiner—Stephen M. Kapner
Attorney, Agent, or Firm—John A. Shedden

[57] ABSTRACT

A compound is disclosed having the structural formula

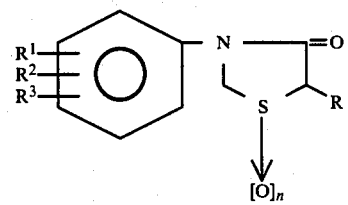

where
R is hydrogen, chlorine, bromine, $C_1-C_4$ alkyl, $C_1-C_4$ alkoxy, —$CH_2COOH$, —$CH_2COO$ ($C_1-C_4$ alkyl), —$CH_2CONHN$ ($C_1-C_2$ alkyl)$_2$, —$CH_2CONR^4R^5$, —$SPS(C_1-C_4$ alkoxy)$_2$ or —$SPO(C_1-C_4$ alkoxy)$_2(C_1-C_4$ alkylthio)$_2$;
$R^1$, $R^2$ and $R^3$ are the same or different and are hydrogen, hydroxy, fluorine, chlorine, bromine, iodine, $C_1-C_6$ alkyl, $C_1-C_6$ alkoxy, $C_1-C_6$ alkylthio, $C_1-C_4$ alkylsulfonyl, $C_1-C_6$ fluoroalkyl, $C_1-C_6$ chloroalkyl, $C_1-C_6$ fluoroalkoxy, $C_1-C_6$ chloroalkoxy, $C_1-C_6$ fluoroalkylthio, $C_1-C_6$ chloroalkylthio, $C_7-C_9$ aralkyl, phenyl, phenoxy, phenylthio, $C_2-C_5$ alkoxycarbonyl, carboxy, nitro or cyano; and
$R^4$ and $R^5$ are the same or different and are hydrogen or $C_1-C_6$ alkyl; alternatively
$R^4$ and $R^5$ together are $C_4-C_6$ alkylene or $C_4-C_6$ oxydialkylene; and
n is 0, 1 or 2.

This compound is useful in regulating the growth of plants and can be formed int a composition, useful in this application. The composition comprises the compound having the structural formula given above and an inert carrier therefor. A process for forming the compound set forth above is also taught.

11 Claims, No Drawings

SUBSTITUTED THIAZOLIDINONES USEFUL AS PLANT GROWTH REGULATORS

BACKGROUND OF THE DISCLOSURE

1. Field of the Invention

The instant invention is directed to a class of substituted thiazolidinones. More specifically, the instant invention is directed to a class of substituted thiazolidinones useful as plant growth regulants.

2. Background of the Prior Art

The importance of plant growth regulants in agriculture has grown in importance over the past few years. The applications to which plant growth regulants are now put includes dwarfing, cessation of terminal growth, inhibition of axillary and intercalary growth, yield increase and the like. These applications have increased useful production of economically important crops and have, in addition, greatly improved the appearance, without the requirement of difficult and expensive manual labor, of ornamental plants.

Thiazolidinone derivatives are known in the prior art. However, there is no prior art disclosing compounds having a unique structure which provides effective plant growth regulation in combination with low phytotoxicity. That is, preferred plant growth regulants retard undesirable plant growth without damaging the plant organism. The substituted thiazolidinones of the prior art usually claim pesticidal properties. Some such compounds are said to have plant growth regulant functionality. However, these compounds do not provide the excellent plant growth regulation desired in combination with low plant phytotoxicity.

SUMMARY OF THE INVENTION

It has now been discovered that a new class of substituted thiazolidinones possess remarkable plant growth regulant properties in combination with low phytotoxicity. That is, the instant invention is directed to a class of compounds whose excellent retardation of vegetative growth is matched with extraordinary low foliar phytotoxicity.

In accordance with the instant invention, a compound of the formula

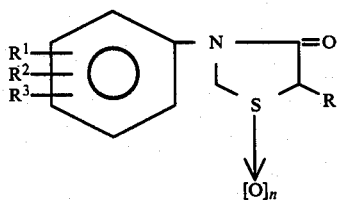

where
R is hydrogen, chlorine, bromine, $C_1$-$C_4$ alkyl, $C_1$-$C_4$ alkoxy, —$CH_2COOH$, —$CH_2COO(C_1$-$C_4$ alkyl), —$CH_2CONHN$ ($C_1$-$C_2$ alkyl)$_2$, —$CH_2CONR^4R^5$, —$SPS(C_1$-$C_4$ alkoxy)$_2$ or —$SPO(C_1$-$C_4$ alkoxy)$_2(C_1$-$C_4$ alkylthio)$_2$;

$R^1$, $R^2$ and $R^3$ are the same or different and are hydrogen, hydroxy, fluorine, chlorine, bromine, iodine, $C_1$-$C_6$ alkyl, $C_1$-$C_6$ alkoxy, $C_1$-$C_6$ alkylthio, $C_1$-$C_4$ alkylsulfonyl, $C_1$-$C_6$ fluoroalkyl, $C_1$-$C_6$ chloroalkyl, $C_1$-$C_6$ fluoroalkoxy, $C_1$-$C_6$ chloroalkoxy, $C_1$-$C_6$ fluoroalkylthio, $C_1$-$C_6$ chloroalkylthio, $C_7$-$C_9$ aralkyl, phenyl, phenoxy, phenylthio, $C_2$-$C_5$ alkoxycarbonyl, carboxy, nitro or cyano;

$R^4$ and $R^5$ are the same or different and are hydrogen or $C_1$-$C_6$ alkyl; alternatively $R^4$ and $R^5$ together are $C_4$-$C_6$ alkylene or $C_4$-$C_6$ oxydialkylene; and n is 0, 1 or 2.

In further accordance with the instant invention, a composition comprising a compound of the formula

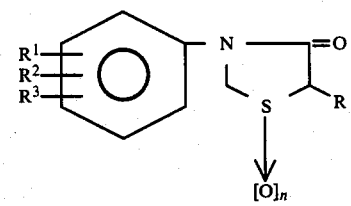

where the meanings of R, $R^1$, $R^2$ and n are as given above and a carrier therefor is taught.

In still further accordance with the instant invention, a process for forming a compound of the formula

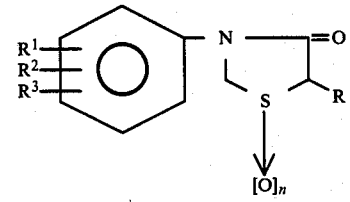

where R, $R^1$, $R^2$ and n has the meanings given above is set forth. In this process an aromatic amine of the formula $ArNH_2$ where Ar represents an aryl group is dissolved in an alcohol and reacted with aqueous formaldehyde and a mercaptocarboxylic acid is set forth.

In yet further accordance with the instant invention, a process for regulating plant growth by applying a plant growth regulant effective amount of a compound of the formula

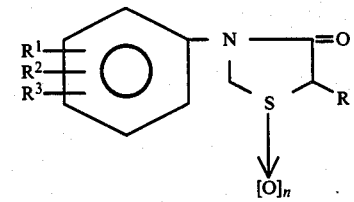

where R, $R^1$, $R^2$ and n has the meanings above is recited.

DETAILED DESCRIPTION

The present invention is directed to a compound having the structural formula

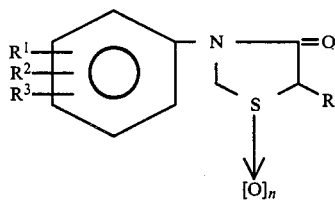

where

R is hydrogen, chlorine, bromine, $C_1$-$C_4$ alkyl, $C_1$-$C_4$ alkoxy, —$CH_2COOH$, —$CH_2COO(C_1$-$C_4$ alkyl), —$CH_2CONHN(C_1$-$C_2$ alkyl)$_2$, —$CH_2CONR^4R^5$, —$SPS(C_1$-$C_4$ alkoxy)$_2$ or —$SPO(C_1$-$C_4$ alkoxy)$_2(C_1$-$C_4$ alkylthio)$_2$;

$R^1$, $R^2$ and $R^3$ are the same or different and are hydrogen, hydroxy, fluorine, chlorine, bromine, iodine, $C_1$-$C_6$ alkyl, $C_1$-$C_6$ alkoxy, $C_1$-$C_6$ alkylthio, $C_1$-$C_4$ alkylsulfonyl, $C_1$-$C_6$ fluoroalkyl, $C_1$-$C_6$ chloroalkyl, $C_1$-$C_6$ fluoroalkoxy, $C_1$-$C_6$ chloroalkoxy, $C_1$-$C_6$ fluoroalkylthio, $C_1$-$C_6$ chloroalkylthio, $C_7$-$C_9$ aralkyl, phenyl, phenoxy, phenylthio, $C_2$-$C_5$ alkoxycarbonyl, carboxy, nitro or cyano;

$R^4$ and $R^5$ are the same or different and are hydrogen or $_1$-$C_6$ alkyl; alternatively $R^4$ and $R^5$ together are $C_4$-$C_6$ alkylene or $C_4$-$C_6$ oxydialkylene; and n is 0, 1 or 2.

More preferably, the instant invention is directed to a compound having the structural formula I where R is hydrogen, chlorine, bromine, $C_1$-$C_4$ alkyl, —$CH_2COOH$, $C_1$-$C_2$ alkoxy, —$CH_2CONHN(C_1$-$C_2$ alkyl)$_2$; —$CH_2COO(C_1$-$C_3$ alkyl) or —$SP(S)(C_1$-$C_2$ alkoxy)$_2$;

$R^1$ is fluorine, chlorine, bromine, trifluoromethyl, trichloromethyl, tribromomethyl or —$CH_2COO(C_1$-$C_4$ alkyl);

$R^2$ is hydrogen, chlorine, bromine $C_1$-$C_2$ alkyl or trifluoromethyl;

$R^3$ is hydrogen; and n is 0 or 2.

Still more preferably, the present invention is directed to a compound having the structural formula I where R is hydrogen, chlorine, bromine, $C_1$-$C_4$ alkyl, $C_1$-$C_4$ alkoxy, —$CH_2COO(C_1$-$C_4$ alkyl), —$CH_2CONHN(C_1$-$C_2$ alkyl)$_2$ or —$SP(S)(C_1$-$C_4$ alkoxy)$_2$;

$R^1$ is 3-fluoro, 3-chloro, 3-bromo, 3-$CF_3$, 3-$CCl_3$, 3-$CBr_3$ or 4-$COO(C_1$-$C_4$ alkyl);

$R^2$ is hydrogen; or $R^2$ is 4-chloro or 4-bromo when R is $C_1$-$C_4$ alkoxy, —$CH_2COO(C_1$-$C_4$ alkyl) or —$CH_2CONHN(C_1$-$C_2$ alkyl)$_2$; or $R^2$ is 4-chloro or 4-bromo when R is $C_1$-$C_4$ alkoxy, $CH_2COO(C_1$-$C_4$ alkyl) or —$CH_2CONHN(C_1$-$C_2$ alkyl)$_2$; or $R^2$ is 5-chloro or 5-bromo when R is hydrogen, chlorine, bromine, $C_1$-$C_4$ alkyl or —$SP(S)(C_1$-$C_4$ alkoxy)$_2$;

$R^3$ is hydrogen; and n is 0 or 2.

Yet still more preferably, the present invention relates to a compound having the structural formula I where R is hydrogen, chlorine, $C_1$-$C_2$ alkyl, $C_1$-$C_2$ alkoxy, —$CH_2COO(C_1$-$C_3$ alkyl) or —$SP(S)(C_1$-$C_2$ alkoxy)$_2$;

$R^1$ is 3-chloro, 3-$CF_3$ or 4-$COO(C_1$-$C_2$ alkyl);

$R^2$ is hydrogen; or $R^2$ is 5-chloro when R is $C_1$-$C_2$ alkoxy or —$CH_2COO(C_1$-$C_3$ alkyl); or $R^2$ is 4-chloro when R is hydrogen, chlorine, $C_1$-$C_2$ alkyl or —$SP(S)(C_1$-$C_2$ alkoxy)$_2$;

$R^3$ is hydrogen; and n is 0.

Even still more preferably the instant invention is concerned with a compound having the structural formula I where R is hydrogen, methyl, $C_1$-$C_2$ alkoxy or —$CH_2COO(C_1$-$C_2$ alkyl)$;

$R^1$ is 3-chloro or 3-$CF_3$;

$R^2$ is hydrogen if $R^1$ is 3-$CF_3$; or $R^2$ is 4-chloro if $R^1$ is 3-chloro and R is $C_1$-$C_2$ alkoxy or —$CH_2COO(C_1$-$C_2$ alkyl); or $R^2$ is 5-chloro if $R^1$ is 3-chloro and R is hydrogen or methyl;

$R^3$ is hydrogen; and n is 0.

The instant invention is also directed to a method for forming the compound whose structural formula is (I) where R, $R^1$, $R^2$ and n have the meanings given above, in which an aromatic amine of the formula $ArNH_2$, where Ar is an aryl group, is reacted with aqueous formaldehyde and a mercaptocarboxylic acid. The aromatic amine is dissolved in an alcoholic medium. Specifically, the alcoholic solvent of the process of this invention is a low boiling solvent miscible with water. Upon reaction, an intermediate, an arylaminomethylmercaptoacetic acid, is formed. This reaction is characterized by the development of an exotherm followed by a return to ambient temperature. The intermediate is dehydrolyzed to produce the thiazolidinone of this invention. The dehydrolysis step is characterized by refluxing with xylene wherein first the alcoholic solvent is removed followed by the removal of water from the intermediate to produce the compound of the present invention.

The process steps of the process of the present invention can be represented by the following chemical reactions, where R has the meaning given for Compound (I):

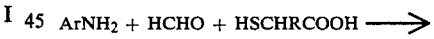

1.

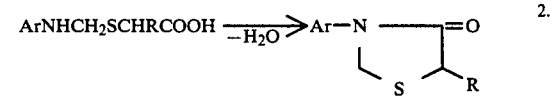

2.

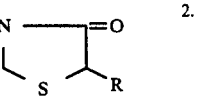

The above procedure produces the compound whose structural formula is (I) with the limitation that n is 0. To produce the corresponding oxide or dioxide, the product of the above process is reacted with an oxidizing agent known in the art. An especially preferred oxidizing agent for this application is m-chloroperoxybenzoic acid. In the case where the oxide is desired (n is 1) the thiazolidinone, the compound having structural formula (I), where n is 0, is reacted with one equivalent of the oxidizing agent. When the dioxide is the desired product (n is 2), the thiazolidinone is reacted with an excess of the oxidizing agent.

It is noted that acetic acid analogs of the product of the present invention may be obtained in the process of the present invention by substituting mercaptosuccinic acid for the mercaptoacetic acid recited above.

The present invention is also directed to a composition useful as a plant growth regulant. The composition of this invention comprises Compound I where R, $R^1$, $R^2$, $R^3$ and n have the meanings given above and an inert carrier therefor.

The carrier, within the contemplation of this composition, may be a finely divided or granular inorganic or inorganic material. Among these are attapulgite clay, sand, vermiculite, corncobs, activated carbon and mineral silicates, such as mica, talc, pyrophyllite and clays.

To form the composition of this invention, Compound I is combined with the inert carrier by methods known in the art. For instance, Compound I, if a solid, is ground into a fine powder and mixed with a powdered carrier within the contemplation of this invention and a surface-active agent. In this embodiment, the thus formed wettable powder is dispersed in water and sprayed onto the plant whose growth is to be regulated. Alternatively, the dispersion is applied to the soil surface in which said plant is grown.

Another embodiment of the composition of this invention entails the preparation of an emulsifiable concentrate. The concentrate is prepared by dissolving Compound I in a suitable solvent such as benzene, toluene or other aliphatic or aromatic hydrocarbon to which a surface active dispersing agent has been added. The emulsifiable concentrate is then dispersed in water and applied by spraying.

Surface active agents suitable for use in the above-described applications are well known to those skilled in the art. McCutecheon's Detergents and Emulsifiers, 1970, Allured Publishing Corp., Ridgewood, N.J. and U.S. Pat. No. 2,514,916, columns 2–4, provide examples of appropriate surface active agents useful in this invention.

The concentration of Compound I, in the composition of this invention, may vary widely. Preferably, the concentration of Compound I represents 1 to 95% by weight based on the total weight of the composition. However, the concentration of Compound I applied as a spray to soil or foliage as a plant growth regulant is in the range of between 0.002 and 75% by weight.

The instant invention is also directed to a method for plant growth regulation which comprises applying a plant growth regulant effective amount of Compound I, where R, $R^1$, $R^2$, $R^3$ and n have the meanings given above, to the locus of the plant to be regulated or the soil in which that plant grows.

In the preferred embodiment, wherein the Compound I is applied to the soil, the compound is applied neat or as a composition of the type described above. Independent of the method of application, the application rate of Compound I to the soil is at a rate of 0.10 to 25 pounds per acre.

The most suitable rate of application is a function of such factors as the particular response desired, the soil type, soil pH, soil organic matter content, wind velocity, quantity and intensity of rainfall before and after treatment, air and soil temperature, light intensity and light duration during the period in which the application is dispensed. All of these factors, including the delivery composition adjuvents, influence the efficacy of Compound I as a plant growth regulant.

The following examples are given to illustrate the scope of the instant invention. Since these examples are given for illustrative purposes only, the scope of this invention should not be limited thereto.

EXAMPLE 1

3-(3,5-Dichlorophenyl)-4-thiazolidinone (Compound 1)

3,5-Dichloroaniline (40.25 g, 0.25 mol) and thioglycolic acid (23 g, 0.25 mol) in ethanol (75 ml) were mixed and stirred. Formaldehyde solution (21.3 ml, 37% by weight) was added to the solution. An exotherm developed and a solid precipitated out. After stirring for several hours, water was added. The solids that had precipitated were collected on a filter, washed with water and air-dried. The product, 2-[[(3,5-dichlorophenyl)amino]methyl]thio]acetic acid (38 g, 0.15 mol), was refluxed in xylene (275 ml). The water formed during refluxing was removed azeotropically. Removal of the solvent left a solid having a melting point of 87°–92° C.

EXAMPLE 2

Preparation of 3-(3,5-dichlorophenyl)-4-thiazolidinone 1,1-dioxide (Compound 2)

3-(3,5-Dichlorophenyl)-4-thiazolidinone (62.5 g, 0.25 mol) formed in accordance with the procedure of Example 1 was dissolved in methylene chloride (50 ml). This solution was stirred while m-chloroperoxybenzoic acid (105 g, 80–85%) in methylene chloride (750 ml) was added dropwise. This procedure was conducted in such a way that the temperature of the reactants did not exceed 20° C. On completion of the addition, the reaction mixture was stirred overnight at ambient temperature. From this reaction mixture the product was extracted with aqueous sodium bicarbonate. The procedure of extraction continued until gassing ceased. Evaporation of the solvent produced the product 3-(3,5-dichlorophenyl)-4-thiazolidinone 1,1-dioxide. The product had a melting point of 175°–177° C. Two similar runs, on twice the scale, gave product having a combined weight of 214 g.

EXAMPLE 3

Preparation of 3-[3-trifluoromethyl)phenyl]-4-thiazolidinone 1,1-dioxide (Compound 5)

3-Aminobenzotrifluoride was converted to 3-[3-(trifluoromethyl)]-4-thiazolidinone in a manner similar to that described in Example 1. The resulting product had a melting point of 53°–54° C. This thiazolidinone (12.5 g, 0.05 mol), dissolved in methylene chloride (25 ml), was cooled to 15°–20° C. M-chloroperoxybenzoic acid (21 g) in methylene chloride (150 ml) was added dropwise. The temperature of the reaction was held below 20° C. After the addition, the reaction mixture was allowed to come to ambient temperature and left stirring overnight. The solid precipitate of this reaction was recrystallized from methanol to give 3-[3-(trifluoromethyl)phenyl]-4-thiazolidinone 1,1-dioxide. The product had a melting point of 115° to 117° C.

The above procedure was repeated so that a total of 1.25 mol of each starting material yielded a total weight of 280 g of product.

EXAMPLE 4

Preparation of ethyl 4-(4-oxo-3-thiazolidinyl)benzoate (Compound 6)

Ethyl p-aminobenzoate (7.3 g) was reacted with 37% formalin (formaldehyde in water) (3.2 ml), mercaptoacetic acid (3.0 ml) and xylene (300 ml). This reaction mixture was refluxed and the water formed thereby was removed azeotropically. After all the water was removed, xylene was evaporated under reduced pressure and the residual oil taken up in methylene chloride. Removal of the methylene chloride solvent left an orange solid which was recrystallized from ethanol to give ethyl 4-(4-oxo-3-thiazolidinyl)benzoate. This product had a melting point of 68°–69° C.

EXAMPLE 5

Preparation of 3-(3,5-dichlorophenyl)-5-methyl-4-thiazolidinone 1-oxide) (Compound 11)

3,5-Dichloroaniline was converted to 3-(3,5-dichlorophenyl)-5-methyl-4-thiazolidinone in accordance with the procedure of Example 4. The only difference was that thiolactic acid was used instead of mercaptoacetic acid. The 3-(3,5-dichlorophenyl)-5-methyl-4-thiazolidinone had a melting point of 80°–88° C. This thiazolidinone (18 g) was oxidized with one equivalent of m-chloroperoxybenzoic acid (14 g) in the same manner as described in Example 2. After removal of the solvent, the reaction product was recrystallized from isopropyl alcohol to yield 3-(3,5-dichlorophenyl)-5-methyl-4-thiazolidinone 1-oxide, m.p. 146°–149° C.

EXAMPLE 6

Preparation of 5-chloro-3-[(3-trifluoromethyl)phenyl]-4-thiazolidinone (Compound 7)

3-[3-(Trifluoromethyl)phenyl]-4-thiazolidinone was converted to its 1-oxide in accordance with the procedure of Example 5. The 1-oxide had a melting point of 120°–123° C. The 21.5 g of the 1-oxide thus formed, in methylene chloride, was cooled in an ice bath before hydrogen chloride gas was added thereto. Upon the introduction of the gas, the reaction mixture went cloudy. When the cloud disappeared and the reaction mixture again cleared it was dried and the solvent removed to leave 5-chloro-3-[3-(trifluoromethyl)phenyl]-4-thiazolidinone, an oil at ambient temperature.

EXAMPLE 7

Preparation of 1-methylethyl 3-(3,4-dichlorophenyl)-4-oxo-5-thiazolidineacetate (Compound 21)

3,4-Dichloroaniline (16.2 g, 0.1 mol) and mercaptosuccinic acid (15 g) were dissolved in xylene (200 ml). While stirring, 37% formalin (8.5 ml) was added followed by heating to reflux. The water formed (9 ml) during this reaction was removed azeotropically. The reaction mixture was filtered hot, befored removing the solvent, to leave an oil, 3-(3,4-dichlorophenyl)-4-oxo-5-thiazolidineacetic acid, which solidified. This crude product was esterified in isopropyl alcohol (500 ml) and concentrated sulfuric acid (3 ml). Removal of the solvent left a crude product which was taken up in methylene chloride, washed with water, dried and evaporated. Recrystallization of the product from toluene/ligroin gave 1-methylethyl 3-(3,4-dichlorophenyl)-4-oxo-5-thiazolidineacetate which had a melting point of 54°–56° C.

EXAMPLE 8

Preparation of 3-(3,4-dichlorophenyl)-5-ethoxy-4-thiazolidinone (Compound 13)

3,4-Dichloroaniline was converted to 3-(3,4-dichlorophenyl)-4-thiazolidinone as outlined in Example 1. This thiazolidinone, which had a melting point of 145°–146° C., was chlorinated with thionyl chloride to form 5-chloro-3-(3,4-dichlorophenyl)-4-thiazolidinone having a melting point of 100°–103° C. Recrystallization of this product from ethanol gave 3-(3,4-dichlorophenyl)-5-ethoxy-4-thiazolidinone which had a melting point of 61°–65° C.

EXAMPLE 9

Preparation of 3-(3,4-dichlorophenyl)-4-oxo-5-thiazolidineacetyl 2,2-dimethylhydrazide (Compound 23)

3-(3,4-Dichlorophenyl)-4-oxo-5-thiazolidineaceacetic acid (73 g) was refluxed in thionyl chloride (100 ml) for two hours before excess thionyl chloride was removed to leave a red oil. This crude acid chloride (10 g) in dimethylformamide (25 ml) was treated with excess 1,1-dimethylhydrazine. An exotherm was observed. When cool, water was added, whereupon a brown solid precipitated out. Recrystallization from ethanol gave 3-(3,4-dichlorophenyl)-4-oxo-5-fhiazolidineacetyl 2,2-dimethylhydrazide having a melting point of 177°–179° C.

EXAMPLE 10

Preparation of ethyl 4-[5-(diethylphosphorothionylthio)-4-oxo-3-thiazolidinyl]benzoate (Compound 26)

Ethyl 4-(4-oxo-3-thiazolidinyl)benzoate, made in accordance with Example 4, was oxidized with one equivalent of m-chloroperoxybenzoic acid to the corresponding 1-oxide. The 1-oxide had a melting point of 117°–120° C. It was converted to ethyl 4-(5-chloro-4-oxo-3-thiazolidinyl)benzoate, having a melting point of 93°–96° C. by the method described in Example 6. Four grams of this benzoate reacted with ammonium diethylphosphorodithioate (2.9 g) in dimethylformamide. The reaction mixture was mixed and stirred overnight at ambient temperature. Water was added and the reaction mixture was extracted with ether. The ether extract was washed with diluted sodium hydroxide, dried and evaporated, to leave ethyl 4-[5-(diethylphosphorothionylthio)-4-oxo-3-thiazolidinyl]benzoate, an oil.

EXAMPLE 11

Preparation of S-[3-(3,4-dichlorophenyl)-4-oxo-5-thiazolidinyl] O,O-diethylphosophorodithioate (Compound 24)

S-[3-(3,4-dichlorophenyl)-4-oxo-5-thiazolidinyl] O,O-diethylphosphorodithioate, an oil, was made in a manner similar to that described in Example 10 using 5-chloro-3-(3,4-dichlorophenyl)-4-thiazolidinone, which was made in accordance with the procedure of Example 9.

EXAMPLE 12

Preparation of S-[3-(3,5-dichlorophenyl)-4-oxo-5-thiazolidinyl] O,O-diothylphosphorodithioate (Compound 25)

S-[3-(3,5-dichlorophenyl)-4-oxo-5-thiazolidinyl] O,O-diethylphosphorodithioate, an oil, was made in a manner similar to that described in Example 10 using 5-chloro-3,-(3,5-dichlorophenyl)-4-thiazolidinone.

EXAMPLE 13

Preparation of Compounds 3, 4, 8–10, 12, 14–20, 22 and 27–135

Additional compounds were prepared using the procedures enumerated in Examples 1–12. All of these additional compounds, Compounds 3, 4, 8–10, 12, 16–20, 22, and 27–135, as well as the compounds formed in accordance with the above examples, characterized by their melting points, having the structural formula I and defined by R, $R^1$, $R^2$, $R^3$ and n, are tabulated in Table I.

TABLE I

| Cpd. No. | R | $R^1$ | $R^2$ | $R^3$ | n | m.p., °C. |
|---|---|---|---|---|---|---|
| 1 | H | 3-Cl | 5-Cl | H | 0 | 87–92 |
| 2 | " | " | " | " | 2 | 175–177 |
| 3 | " | 3-CF$_3$ | H | " | 0 | 53–54 |
| 4 | " | " | " | " | 1 | 120–123 |
| 5 | " | " | " | " | 2 | 115–117 |
| 6 | " | 4-COOC$_2$H$_5$ | " | " | 0 | 68–69 |
| 7 | Cl | 3-CF$_3$ | " | " | 0 | oil |
| 8 | " | 3-Cl | 5-Cl | " | 0 | 115–119 |
| 9 | " | " | " | " | 1 | 145 |
| 10 | CH$_3$ | " | " | " | 0 | 80–83 |
| 11 | " | " | " | " | 1 | 146–149 |
| 11a | " | " | " | " | 2 | 142–144 |
| 12 | OCH$_3$ | 3-CF$_3$ | H | " | 0 | 61–62 |
| 13 | OC$_2$H$_5$ | 3-Cl | 4-Cl | " | 0 | 61–65 |
| 14 | " | 3-CF$_3$ | H | " | 0 | 46–47 |
| 15 | " | 4-COOC$_2$H$_5$ | " | " | 0 | 80–82 |
| 16 | CH$_2$COOCH$_3$ | 3-CF$_3$ | " | " | 0 | 78–79 |
| 17 | " | " | " | " | 1 | 128–130 |
| 18 | " | " | " | " | 2 | 76–77 |
| 19 | " | 3-Cl | 4-Cl | " | 0 | 63–66 |
| 20 | CH$_2$COOC$_2$H$_5$ | " | " | " | 0 | 62–65 |
| 21 | CH$_2$COOCH(CH$_3$)$_2$ | " | " | " | 0 | 54–56 |
| 22 | CH$_2$COOC$_3$H$_7$ | " | " | " | 0 | 43–44 |
| 23 | CH$_2$CONHN(CH$_3$)$_2$ | " | " | " | 0 | 177–179 |
| 24 | SP(S)(OC$_2$H$_5$)$_2$ | " | " | " | 0 | oil |
| 25 | " | " | 5-Cl | " | 0 | oil |
| 26 | " | 4-COOC$_2$H$_5$ | H | " | 0 | oil |
| 27 | H | H | H | " | 0 | 116–119 |
| 28 | " | " | " | " | 1 | 137–138 |
| 29 | " | " | " | " | 2 | 200–204 |
| 30 | " | 2-F | " | " | 0 | 135–140* |
| 31 | " | " | " | " | 1 | 161–163 |
| 32 | " | " | " | " | 2 | 207–209 |
| 33 | " | 3-BR | " | " | 0 | 93–95 |
| 34 | " | " | " | " | 1 | 155–156 |
| 35 | " | " | " | " | 2 | 176–179 |
| 36 | " | 3-I | " | " | 2 | 206–208 |
| 37 | " | 4-F | " | " | 0 | 73–75 |
| 38 | " | " | " | " | 1 | 127–130 |
| 39 | " | " | " | " | 2 | 207–208 |
| 40 | " | 2-Cl | 4-Cl | " | 0 | 101–107 |
| 41 | " | " | " | " | 1 | 112–114 |
| 42 | " | " | " | " | 2 | 197–200 |
| 43 | " | " | 5-Cl | " | 0 | 107–112 |
| 44 | " | " | " | " | 1 | 157–159 |
| 45 | " | 3-Cl | 4-Cl | " | 0 | 145–146 |
| 46 | " | " | " | " | 1 | 156–159 |
| 47 | " | " | " | " | 2 | 188–190 |
| 48 | " | " | 5-Cl | " | 1 | 174–176 |
| 49 | " | 2-Cl | 2-CF$_3$ | " | 0 | 82–84 |
| 50 | " | 2-CF$_3$ | H | " | 0 | 100–103 |
| 51 | " | " | " | " | 1 | 124–126 |
| 52 | " | " | " | " | 2 | 140–142 |
| 53 | " | 4-CF$_3$ | " | " | 0 | 148–152* |
| 54 | " | " | " | " | 1 | 165–166 |
| 55 | " | " | " | " | 2 | 242–244 |
| 56 | " | 4-t-C$_4$H$_9$ | " | " | 0 | 106–109 |
| 57 | " | " | " | " | 1 | 168–170 |
| 58 | " | " | " | " | 2 | 132–140 |
| 59 | " | 2-CH$_2$C$_6$H$_5$ | " | " | 0 | 135–136 |
| 60 | " | " | " | " | 2 | 193–195 |
| 61 | " | 4-CH$_2$C$_6$H$_5$ | " | " | 0 | 101–102 |
| 62 | " | " | " | " | 1 | 147–148 |
| 63 | " | " | " | " | 2 | 158–159 |
| 64 | " | 2-C$_6$H$_5$ | " | " | 0 | oil |
| 65 | " | " | " | " | 1 | 127–130 |
| 66 | " | " | " | " | 2 | 203–205 |
| 67 | " | 2-OCH$_3$ | " | " | 0 | 57–60 |
| 68 | " | " | " | " | 1 | 156–158 |
| 69 | " | " | " | " | 2 | 169–171 |

TABLE I-continued

| Cpd. No. | R | R$^1$ | R$^2$ | R$^3$ | n | m.p., °C. |
|---|---|---|---|---|---|---|
| 70 | " | 3-OCH$_3$ | " | " | 0 | 165–169** |
| 71 | " | " | " | " | 1 | 105–107 |
| 72 | " | " | " | " | 2 | 102–105 |
| 73 | " | 4-OCH$_3$ | " | " | 0 | 95–98 |
| 74 | " | " | " | " | 1 | 115–120 |
| 75 | " | " | " | " | 2 | 179–181 |
| 76 | " | 3-OC$_2$H$_5$ | " | " | 0 | 67–69 |
| 77 | " | " | " | " | 1 | 95–96 |
| 78 | " | " | " | " | 2 | 106–108 |
| 79 | " | 3-SCH$_3$ | " | " | 0 | oil |
| 80 | " | 3-SO$_2$CH$_3$ | " | " | 2 | 172–176 |
| 81 | " | 4-OC$_6$H$_5$ | " | " | 0 | 95–96 |
| 82 | " | " | " | " | 1 | 142–144 |
| 83 | " | " | " | " | 2 | 204–206 |
| 84 | " | 3-COOH | " | " | 0 | 198–204 |
| 85 | " | 4-COOH | " | " | 0 | oil |
| 86 | " | 4-COOC$_2$H$_5$ | " | " | 1 | 117–120 |
| 87 | " | " | " | " | 2 | 149–153 |
| 88 | " | 3-COOC$_6$H$_5$ | " | " | 0 | oil |
| 89 | " | " | " | " | 2 | 166–168 |
| 90 | " | 4-COOC$_6$H$_5$ | " | " | 2 | 222–224 |
| 91 | " | 2-CH$_3$ | 3-Cl | " | 0 | 87–92 |
| 92 | " | " | " | " | 1 | 146–149 |
| 93 | " | " | 6-CH$_3$ | " | 0 | 71–76 |
| 94 | " | 2-C$_2$H$_5$ | 6-C$_2$H$_5$ | " | 0 | 74–76 |
| 95 | " | 2-NO$_2$ | H | " | 0 | 90–93 |
| 96 | " | " | " | " | 2 | 170–172 |
| 97 | " | 4-NO$_2$ | " | " | 0 | 144–145 |
| 98 | " | " | " | " | 1 | oil |
| 99 | " | " | " | " | 2 | 169–170 |
| 100 | " | 2-CN | " | " | 0 | 120–122 |
| 101 | " | " | " | " | 1 | 161–163 |
| 102 | " | " | " | " | 2 | 154–164 |
| 103 | " | 3-CN | " | " | 0 | 98–100 |
| 104 | " | " | " | " | 1 | 128–130 |
| 105 | " | " | " | " | 2 | 197–200 |
| 106 | Cl | 2-Cl | 5-Cl | " | 0 | 153–155 |
| 107 | " | 3-Cl | 4-Cl | " | 0 | 104–109 |
| 108 | " | 4-COOC$_2$H$_5$ | H | " | 0 | 93–96 |
| 109 | CH$_3$ | 2-Cl | 4-Cl | " | 0 | 76–78 |
| 110 | " | 3-Cl | " | " | 0 | 109–115 |
| 111 | " | " | " | " | 1 | 100–107 |
| 112 | " | 2-CF$_3$ | H | " | 0 | oil |
| 113 | " | 3-OC$_2$H$_5$ | " | " | 0 | 50–52 |
| 114 | " | " | " | " | 1 | oil |
| 115 | " | " | " | " | 2 | 81–82 |
| 116 | CH$_3$O | 3-Cl | 4-Cl | " | 0 | 133–135 |
| 117 | i-C$_3$H$_7$O | 2-Cl | 5-Cl | " | 0 | 103–107 |
| 118 | CH$_2$COOH | 3-Cl | 4-Cl | " | 0 | 151–152 |
| 119 | " | " | " | " | 1 | oil |
| 120 | " | 2-Cl | 5-CF$_3$ | " | 0 | 109–111 |
| 121 | " | 3-CF$_3$ | H | " | 0 | 123–127 |
| 122 | " | 4-OCH$_3$ | " | " | 0 | 163–167 |
| 123 | " | 4-COOC$_2$H$_5$ | " | " | 0 | 143–147 |
| 124 | CH$_2$COOC$_2$H$_5$ | 3-Cl | 4-Cl | " | 1 | 112–114 |
| 125 | " | " | " | " | 2 | 122–123 |
| 126 | " | 3-CF$_3$ | H | " | 0 | 66–69 |
| 127 | CH$_2$COOiC$_3$H$_7$ | 3-Cl | 4-Cl | " | 1 | 153–154 |
| 128 | " | " | " | " | 2 | 133–134 |
| 129 | SPS(OCH$_3$)$_2$ | 2-Cl | 5-Cl | " | 0 | oil |
| 130 | " | " | 5-CF$_3$ | " | 0 | oil |
| 131 | " | 3-CF$_3$ | H | " | 0 | oil |
| 132 | " | 4-COOC$_2$H$_5$ | " | " | 0 | oil |
| 133 | SPS(OC$_2$H$_5$)$_2$ | 3-CF$_3$ | " | " | 0 | oil |
| 134 | SPO(OC$_2$H$_5$(SC$_3$H$_7$) | " | " | " | 0 | oil |
| 35 | CH$_2$CON[ring with CH$_3$, O, CH$_3$] | Cl | Cl | " | 0 | 149–150 |

*At 0.05 mm Hg.
**At 0.1 mm Hg.

EXAMPLE 14

NMR Characterization of Compds 7, 24–26, 64, 79, 85, 88, 98, 112, 114, 119 and 129–134

Those compounds included in Table I which could not be characterized by their melting points, because they are oils at atmospheric conditions, were characterized by nuclear magnetic resonance (NMR) techniques known in the art. The resultant NMR data is summarized in Table II.

TABLE II

| Compound No. | Solvent | Characteristics (Lambda Values) |
|---|---|---|
| 7 | CDCl$_3$ | 7.2–8.0(4H,m), 5.2(1H,s), 5.2–5.3(1H,d), 4.7–4.8(1H,d) |
| 24 | CDCl$_3$ | 7.0–7.6(3H,m), 5.2(1H,s), 4.85–5.0(1H,d), 4.4–5.55(1H,d), 3.8–4.9(4H,m), 1.0–1.4(6H,m) |
| 25 | CDCl$_3$ | 7.1–7.4(3H,m), 5.3(1H,s), 4.9–5.1(1H,d), 4.7–4.8(1H,d), 3.9–4.4(4H,m), 1.0–1.4(6H,m) |
| 26 | CDCl$_3$ | 7.4–8.0(4H,m), 5.3(1H,s), 4.85–5.05(1H,d), 4.6–4.7(1H,d), 3.8–4.4(6H,m), 0.9–1.3(9H,m) |
| 64 | CDCl$_3$ | 7.4(9H,s), 4.15(2H,s), 3.55(2H,s) |
| 79 | CDCl$_3$ | 7.0–7.5(4H,m) 4.8(2H,s), 3.75(2H,s), 2.5(3H,s) |
| 85 | DMSO-D$_6$ | 7.6–8.1(4H,m), 5.0(2H,s), 3.7(2H,s) |
| 88 | CDCl$_3$ | 7.0–8.2(9H,m), 4.75(2H,s), 3.65(2H,s) |
| 98 | DMSO-D$_6$ | 7.78–8.4(4H,m), 5.0–5.15(2H,d) 3.9–4.15(2H,d) |
| 112 | CDCl$_3$ | 6.9–8.5(4H,m), 5.0–5.5(2H,m), 3.5–3.9(1H,t), 1.5–1.7(3H,d) |
| 114 | CDCl$_3$ | 6.4–7.5(4H,m), 4.3–4.7(2H,m), 3.7–4.3(2H,m), 3.3–3.7(1H,t), 1.1–1.7(6H,m) |
| 119 | TFA | 7.2–7.7(3H,m), 5.0–5.3(2H,d), 4.5–4.7(1H,m), 3.4–3.6(2H,m) |
| 129 | CDCl$_3$ | 7.0–7.5(3H,m), 2.35(6H,s) |
| 130 | CDCl$_3$ | 7.5–7.7(3H,s), 4.5–5.0(2H,m), 3.55–3.9(6H,d) |
| 131 | CDCl$_3$ | 7.3–8.0(4H,m), 4.7–5.2(1H,q), 3.5–4.0(2H,d), 2.8–3.0(6H,d) |
| 132 | CDCl$_3$ | 7.4–8.0(4H,m), 4.0–5.2(5H,m), 3.55–3.85(6H,d), 1.1–1.3(3H,t) |
| 133 | CDCl$_3$ | 7.2–7.8(4H,m), 5.2–5.45(1H,d), 4.9–5.1(1H,d), 4.6–4.8(1H,d), 4.0–4.4(4H,m), 1.2–1.5(6H,m) |
| 134 | CDCl$_3$ | 7.2–7.8(4H,m), 4.0–5.3(7H,m), 0.8–1.9(8H,m) |

REMARKS
CDCl$_3$ - Deuterated Chloroform
DMSO-D$_6$ - Deuterated Dimethylsulfoxide
TFA - Trifluoroacetic Acid

EXAMPLE 15

Use of Compounds 1–26 as Plant Growth Regulants

Each of Compounds 1–26, summarized in Table I, were made into solutions by dissolving 600 mg of the compounds in 10 ml of an organic solvent. In most cases, the organic solvent used was acetone. Thirty milligrams of the emulsifying agent, "Tween 20" (a trademark for ethoxylated sorbitan monolaurate) was added to the solution. To this was added 100 ml of distilled water to form an emulsion, having a concentration of 6,000 ppm of the active agent (Compounds 1–26). Twenty milliliters of the 6,000 ppm emulsion were diluted to 120 ml with the addition of 100 ml distilled water resulting in an emulsion having a concentration of 1,000 ppm.

The 1,000 and 6,000 ppm emulsions were sprayed onto foliage of 2-week old soybean plants (Glycine max (L.) Merr cv. Williams) to the drip point. The emulsion was applied as an atomized spray with a DeVilbiss (trademark) No. 152 sprayer. The sprayed plants were then placed in a greenhouse for three weeks. The plants were scored for retardation of vegetative growth and for foliar phytotoxicity.

Foliar phytotoxicity was scored on a 0 to 100 scale where 0 represented absolutely no damage and 100 represented complete destruction of the plant. As a guide, the rating system of Frans & Talbert (Research Methods in Weed Science, 2nd Edition, Southern Weed Science Society, 1977) was used.

The effect of plant retardation and phytotoxicity on the soybean plants, as a result of treatment with Compounds 1–26, are summarized in Table III.

TABLE III

| | Retardation of Soybeans | | | |
|---|---|---|---|---|
| | % Retardation at | | % Phytotoxicity at | |
| Cpd. No. | 6000 ppm | 1000 ppm | 6000 ppm | 1000 ppm |
| 1 | 0 | 48 | 85 | 2 |
| 2 | 90 | 30 | 15 | 0 |
| 3 | 0 | 47 | 90 | 27 |
| 4 | 19* | 3 | 4* | 3 |
| 5 | 95 | 16 | 5 | 20 |
| 6 | 25 | 0 | 55 | 0 |
| 7 | 20 | 0 | 5 | 0 |
| 8 | 24* | 1 | 4* | 2 |
| 9 | 10 | 0 | 0 | 0 |
| 10 | 0 | 11 | 40 | 0 |
| 11 | 80 | 7 | 0 | 0 |
| 11a | 0 | 11 | 0 | 0 |
| 12 | 52* | 16 | 12* | 3 |
| 13 | 80 | 20 | 40 | 10 |
| 14 | 16* | 0 | 4* | 3 |
| 15 | 20 | 0 | 0 | 0 |
| 16 | 47* | 0 | 3* | 3 |
| 17 | 10* | 0 | 4* | 3 |
| 18 | 12* | 3 | 3* | 3 |
| 19 | 39* | 5 | 4* | 2 |
| 20 | 23* | 2 | 3* | 3 |
| 21 | 60 | 7 | 10 | 0 |
| 22 | 13* | 5 | 2* | 1 |
| 23 | 20 | 0 | 0 | 0 |
| 24 | 90 | 30 | 0 | 0 |
| 25 | 90 | 20 | 5 | 0 |
| 26 | 20 | 0 | 0 | 0 |

*tested at 3000 pm. concentration.

EXAMPLE 16

Effect on Plant Height and Production (Compds 2, 7, 11, 13, 21)

Five of the compounds listed in Table III were tested to determine their effect on soybean plant height and number of pods formed. To accomplish this, additional three-week old soybean plants (Glycine max (L.) Merr. cv. Williams) were sprayed with 6,000 ppm emulsions of Compounds 2, 7, 11, 13 and 21. In addition, a control, untreated with any plant growth regulant, was employed. The so-treated soybean plants, along with the control untreated with any plant growth regulant, were all placed in a greenhouse until the mature green pod stage was reached (ca. 8 to 12 weeks). At that time, the plants were inspected to determine their height and the number of pods formed. The results of this test is summarized in Table IV below.

TABLE IV

| Cpd. No. | Plant Height (cm) | No. of Pods per Plant | Weight of Pods |
|---|---|---|---|
| 2 | 104 | 51 | 54 |
| 7 | 142 | 42 | 51 |
| 11 | 189 | 47 | 59 |
| 13 | 86 | 52 | 71 |
| 21 | 93 | 48 | 50 |
| Control | 207 | 43 | 52 |

*Green Weight

The data indicate that the plant growth regulant decreases the size of the soybean plants but, surprisingly, increases the number of useful pods per plant compared to the number produced on the uncontrolled plant.

EXAMPLE 17

Effect on Plant Height and Production (Comp'd 53)

The procedure of Example 16 was repeated except that Compound No. 53, as defined in Table I, was utilized. Moreover, rather than a concentration of 6,000 ppm, Compound 53 was applied to soybean plants as an emulsion in concentrations of 3,000 ppm, 750 ppm and 188 ppm. In addition, a soybean plant control was grown under the same conditions as the tested compounds without application of Compound 53. The results of this test are summarized in Table V.

TABLE V

| Cpd. No. | Dosage (ppm) | Plant Height (cm) | No. of pods | Weight of pods (g)* |
|---|---|---|---|---|
| 53 | 3000 | 52 | 9.8 | 6.9 |
| 53 | 750 | 83 | 20.5 | 9.8 |
| 53 | 188 | 103 | 21.3 | 9.5 |
| None | | 128 | 15.8 | 8.9 |

*Dry Weight

The data indicate that the compound of this invention reduced plant height by as much as 59%, but increased the number and weight of pods at the lower dosages by 35% and 10%, respectively.

The preferred embodiments and examples given above illustrate the scope and spirit of this invention. These embodiments and examples will suggest, to those skilled in the art, other embodiments and examples. These other embodiments and examples are within the contemplation of the present invention. Therefore, the instant invention should be limited only by the appended claims.

What is claimed is:

1. A compound having the structural formula

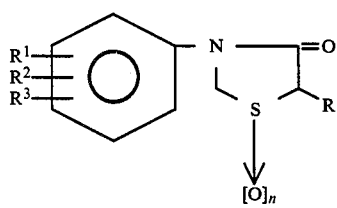

where

R is hydrogen, chlorine, bromine, $C_1$-$C_4$ alkyl, $C_1$-$C_4$ alkoxy, —$CH_2COOH$, —$CH_2COO(C_1$-$C_4$ alkyl), —$CH_2CONHN(C_1$-$C_2$ alkyl)$_2$; —$CH_2CONR^4R^5$, —$SPS(C_1$-$C_4$ alkoxy)$_2$ or —$SPO(C_1$-$C_4$ alkoxy)($C_1$-$C_4$ alkylthio);

$R^1$ and $R^2$ are the same or different and are hydrogen, fluorine, chlorine, bromine, iodine or $C_1$-$C_6$ alkyl;

$R^3$ is hydrogen, fluorine, chlorine, bromine, iodine, $C_1$-$C_6$ alkyl, $C_1$-$C_6$ alkoxy, $C_1$-$C_6$ alkylthio, $C_1$-$C_4$ alkylsulfonyl, $C_1$-$C_6$ fluoroalkyl, $C_1$-$C_6$ chloroalkyl, $C_1$-$C_6$ fluoroalkoxy, $C_1$-$C_6$ chloroalkoxy, $C_1$-$C_6$ fluoroalkylthio, $C_1$-$C_6$ chloroalkylthio, $C_7$-$C_9$ phenylalkyl, phenyl, phenoxy, phenylthio, $C_2$-$C_5$ alkoxycarbonyl, carboxy, nitro or cyano; and $R^4$ and $R^5$ are the same or different and are hydrogen or $C_1$-$C_6$ alkyl; alternatively $R^4$ and $R^5$ together are $C_4$-$C_6$ alkylene or $C_4$-$C_6$ oxydialkylene; and n is 0, 1 or 2;

with the proviso that $R^1$, $R^2$ and $R^3$ cannot all be hydrogen.

2. A compound in accordance with claim 1 where

R is hydrogen, chlorine, bromine, $C_1$-$C_4$ alkyl, $C_1$-$C_4$ alkoxy, —$CH_2CONHN(C_1$-$C_2$ alkyl)$_2$, —$CH_2COO(C_1$-$C_4$ alkyl) or —$SP(S)$ ($C_1$-$C_2$ alkoxy)$_2$;

$R_3$ is fluorine, chlorine, bromine, trifluoromethyl, trichloromethyl, tribromomethyl or $CH_2COO(C_1$-$C_4$ alkyl);

$R^2$ is hydrogen, chlorine, bromine or $C_1$-$C_2$ alkyl;

$R^1$ is hydrogen; and n is 0 or 2.

3. A compound in accordance with claim 2 where

R is hydrogen, chlorine, bromine, $C_1$-$C_4$ alkyl, $C_1$-$C_2$ alkoxy, —$CH_2CONHN(C_1$-$C_2$ alkyl)$_2$, —$CH_2COO(C_1$-$C_4$ alkyl) or —$SP(S)$ ($C_1$-$C_4$ alkoxy)$_2$;

$R^3$ is 3-fluoro, 3-chloro, 3-bromo, 4-$CF_3$, 3-$CCl_3$, 3-$CBr_3$ or 4-$COO(C_1$-$C_4$ alkyl);

$R^2$ is hydrogen; or $R^2$ is 4-chloro or 4-bromo when R is $C_1$-$C_4$ alkoxy, —$CH_2COO(C_1$-$C_4$ alkyl) or —$CH_2CONHN(C_1$-$C_2$ alkyl)$_2$; or $R^2$ is 4-chloro or 4-bromo when R is $C_1$-$C_4$ alkoxy, —$CH_2COO(C_1$-$C_4$ alkyl) or —$CH_2CONHN(C_1$-$C_2$ alkyl)$_2$; or $R^2$ is 5-chloro or 5-bromo when R is hydrogen, chlorine, bromine, $C_1$-$C_4$ alkyl or —$SP(S)$ ($C_1$-$C_4$ alkoxy)$_2$.

4. A compound in accordance with claim 3 where

R is hydrogen, chlorine, $C_1$-$C_2$ alkyl, $C_1$-$C_2$ alkoxy, —$CH_2COO(C_1$-$C_3$ alkyl) or —$SP(S)$ ($C_1$-$C_2$ alkoxy)$_2$;

$R^3$ is 3-chloro, 3-$CF_3$ or 4-$COO(C_1$-$C_2$ alkyl);

$R^2$ is hydrogen; or $R^2$ is 5-chloro when R is $C_1$-$C_2$ alkoxy or —$CH_2COO(C_1$-$C_3$ alkyl); or $R^2$ is 4-chloro when R is hydrogen, chlorine, $C_1$-$C_2$ alkyl or —$SP(S)$ ($C_1$-$C_2$ alkoxy)$_2$; and n is 0; or n is 2 if R is hydrogen, chlorine, $C_1$-$C_2$ alkyl or —$SP(S)$ ($C_1$-$C_2$ alkoxy)$_2$.

5. A compound in accordance with claim 4 where

R is hydrogen, methyl, $C_1$-$C_2$ alkoxy or —$CH_2COO(C_1$-$C_2$ alkyl);

$R^3$ is 3-chloro or 3-$CF_3$;

$R^2$ is hydrogen if R is 3-$CF_3$; or $R^2$ is 4-chloro if $R^1$ is 3-chloro and R is $C_1$-$C_2$ alkoxy or —$CH_2COO(C_1$-$C_2$ alkyl); or $R^2$ is 5-chloro if $R^1$ is 3-chloro and R is hydrogen or methyl; and n is 0.

6. A composition comprising the compound of claim 1 and an inert carrier therefor.

7. A composition comprising the compound of claim 2 and an inert carrier therefor.

8. A composition comprising the compound of claim 3 and an inert carrier therefor.

9. A method of regulating the growth of plants comprising applying to the locus of the plant to be regulated an effective plant regulating amount of the compound of claim 1.

10. A method of regulating the growth of plants comprising applying to the locus of the plant to be regulated an effective plant regulating amount of the compound of claim 2.

11. A method of regulating the growth of plants comprising applying to the locus of the plant to be regulated an effective plant regulating amount of the compound of claim 3.

* * * * *